United States Patent [19]

Auerbach

[11] Patent Number: 4,801,777
[45] Date of Patent: Jan. 31, 1989

[54] BLOOD REWARMING METHOD AND APPARATUS

[75] Inventor: Paul S. Auerbach, Brentwood, Tenn.

[73] Assignee: Vanderbilt University, Nashville, Tenn.

[21] Appl. No.: 92,468

[22] Filed: Sep. 3, 1987

[51] Int. Cl.$^4$ .............................................. H05B 6/80
[52] U.S. Cl. ..................... 219/10.55 M; 219/10.55 F; 604/114; 604/409
[58] Field of Search ................ 219/10.55 M, 10.55 R, 219/10.55 F, 10.55 E; 604/113, 114, 403, 408, 409; 128/399, 804

[56] References Cited

U.S. PATENT DOCUMENTS

| | | | |
|---|---|---|---|
| 2,845,929 | 8/1958 | Strumia | 604/113 |
| 3,219,460 | 11/1965 | Brown | 219/10.55 E |
| 3,335,253 | 8/1967 | Jeppson et al. | 219/10.55 A |
| 3,398,251 | 8/1968 | Jeppson et al. | 219/10.41 |
| 3,427,422 | 2/1969 | Müller | 219/10.55 R |
| 3,518,393 | 6/1970 | Besseling et al. | 219/10.41 |
| 3,809,845 | 5/1974 | Stenstrom | 219/10.55 R |
| 3,814,889 | 6/1974 | Stenstrom | 219/10.55 M |
| 4,091,119 | 5/1978 | Bach | 426/234 |
| 4,122,324 | 10/1978 | Falk | 219/10.55 E |
| 4,228,945 | 10/1980 | Wysocki | 229/30 |
| 4,280,032 | 7/1981 | Levinson | 219/10.55 E |
| 4,283,427 | 8/1981 | Winters et al. | 126/107 |
| 4,316,070 | 2/1982 | Prosise et al. | 219/10.55 E |
| 4,336,435 | 6/1982 | Kashyap et al. | 219/10.55 F |
| 4,345,133 | 8/1982 | Chernex et al. | 219/10.55 E |
| 4,351,997 | 9/1982 | Mattisson | 219/10.55 E |
| 4,413,167 | 11/1983 | Martel et al. | 219/10.55 E |
| 4,439,656 | 3/1984 | Peleg | 219/10.55 M |
| 4,503,307 | 3/1985 | Campbell et al. | 219/10.55 F |
| 4,622,140 | 11/1986 | Lee et al. | 210/177 |
| 4,652,712 | 3/1987 | Zeipel | 219/10.55 F |

OTHER PUBLICATIONS

Linko, K. et al., Erythrocyte Damage Caused by the Haemotherm Microwave Blood Warmer, Acta Anaesth, Scand. (1979), vol. 23, 320-328.
Staples, P. J. et al., Extracorporeal Hemolysis of Blood in a Microwave Blood Warmer, N.E. Jour. Of Med. (1971), vol. 285, 317-319.
Arens, J. F. et al., Danger of Overwarming Blood by Microwave, JAMA (1971), vol. 218, 1045-1046.
Leaman, P. G. et al., Microwave Warming of Resuscitation Fluids, Annals of Emerg. Med. (1985), vol. 14 876-879.
Dalili, H. et al., Effects of Various Blood Warmers on the Components of Bank Blood, Anesth. & Analg. (1974), vol. 53, 125-131.
McCullough, J. et al., Iatrogenic Hemolysis: A Complication of Blood Warmed by a Microwave Device, Anesth. & Analg. (1972), vol. 51, 102-106.

Primary Examiner—Philip H. Leung
Attorney, Agent, or Firm—Tilton, Fallon, Lungmus

[57] ABSTRACT

A method and apparatus for rewarming blood (including refrigerated whole blood, packed red blood cells, and fresh frozen plasma) in which the temperature of the blood is quickly raised to infusion temperature without hemolysis or other damage to its constituents. The blood, contained in a conventional blood administration bag, is subjected to microwave irradiation while being totally immersed in a body of water. Structure is provided for immobilizing the blood bag within the body of water, and a sensor detects when a desired temperature has been attained and causes automatic cessation of microwave generation. The immobilizing structure may also be provided with a microwave-opaque barrier for shielding certain portions of a blood bag against excessive radiation exposure. A pump may also be provided for circulation of the water within the apparatus.

22 Claims, 2 Drawing Sheets

BLOOD REWARMING METHOD AND APPARATUS

BACKGROUND AND SUMMARY

It is well recognized that rapid transfusion of multiple units of refrigerated (standardly, at 4 degrees C.) blood (whole blood, packed red blood cells, or fresh frozen plasma) without rewarming such blood to body temperature can be hazardous, causing hypothermia, cardiac arrhythmias, and coagulopathy. Cold whole blood and packed red blood cells are more viscous than warmed products, and do not achieve the same rates of flow, which decreases the rate of administration. Fresh frozen plasma, which is stored frozen, requires 20 to 30 minutes for thawing and rewarming by currently-utilized techniques.

A number of techniques have been attempted for blood rewarming, including direct heating, water-bath-/coil heating, and microwave heating. Of these, the only successful method to date has been the water bath technique in which blood is passed through coiled tubing immersed in a temperature-controlled water bath. The blood is carried through the tubing by gravity or by a mechanical pump. While that technique is reliable to the extent that it avoids overheating of the blood, it carries a number of disadvantages. The apparatus required for providing rapid transfusion of multiple units is expensive in terms of both initial costs and operating costs. The equipment is unwieldy, inconvenient to use, and only marginally portable since the entire water bath must be transportable. Because of its cumbersome nature, such equipment is often unmanageable in emergency departments and operating rooms. Finally, larger blood warming equipment generally requires that the blood utilized first be "donated" to the equipment so that if multiple units are not transfused they become wasted.

For these reasons, and because conventional water-bath/coil/pump systems require costly priming and considerable set-up time, efforts began in the mid-1960's to develop microwave warmers for rapid heating of blood in plastic bags then (and currently) in widespread use worldwide. While initially met with enthusiasm, these methods have been denounced and abandoned, largely because of problems of differential excessive heating which caused red cells to hemolyze, rendering them useless for transfusion. Despite considerable developmental effort, the problems of differential heating could not be solved by mechanical agitation or by rotating cylinders used to effect constant admixture. Segments of narrow diameter tubing, which are integral parts of blood storage bags, frequently overheated and even exploded. Quality control to avoid overheating was considered impossible because of variability in the volume of blood units and effective temperature/time surveillance. Microwave rewarming of fresh frozen plasma (in contrast to that of whole blood and packed red cells) has been achieved successfully, but the technique is complicated, involving steps of first softening the bag and its contents under warm running water, followed by sealing and removal of all tubing to avoid bursting. The bag is then dried and placed in a plastic overbag, protecting all metal clips and remaining narrow tubulature. Microwave exposure is applied in short (10 second) increments under constant observation until the thaw is completed. At the conclusion, the plasma still remains considerably below body temperature. Because of the complexity of this technique, most blood banks continue to utilize the water bath method for thawing plasma.

Investigators have demonstrated that microwave energy does not appear to be intrinsically harmful to blood in vitro or in vivo as long as the temperature does not reach the point at which hemolysis occurs. Microwave energy does not appreciably affect the survival or activity of red cells, nor does it render the coagulation factors in plasma less effective, as determined by chemistry/electrolyte determinations, radioactive chromium tags, serum haptoglobin and adenosine triphosphate measurements. The major difficulty that has led to the abandonment of microwave energy utilization for rewarming banked blood has been the conversion of microwave energy to heat without overheating the blood products.

An important aspect of this invention therefore lies in the discovery that it is indeed possible to thaw and/or warm banked blood using microwave energy in a controlled method without inflicting damage to the constituents of that blood. Compared with conventional water-bath/coil/pump systems, the method and apparatus of this invention involve zero set-up time, 5 to 6 minute warming time for refrigerated whole blood or packed red blood cells and 7 to 8 minute warming time for FFP, a high degree of mobility of the apparatus (since no water connections are needed), minimal storage and operating space, relatively low capital investment, and negligible operating expense. The method and apparatus of this invention eliminate the complications previously encountered with microwave heating of blood, with tests revealing that the warmed product is free from hemolysis occasioned by localized overheating and retains all of the properties of fresh stored blood.

The term "blood" as used herein is intended to include not only refrigerated whole blood but also the separated and/or treated components of whole blood. Accordingly, the term includes both packed red blood cells (PRBC) and fresh frozen plasma (FFP), all of which are routinely processed and stored in blood banking operations. Particularly in the United States, but in other countries as well, such blood is placed in plastic bags or pouches for storage and subsequent infusion, all well-understood in the health care field.

Briefly, the apparatus and method involve supporting a blood bag in a microwave-transmissible housing containing a body of water and then immobilizing the blood bag so that water completely surrounds the stationary bag. The water and bag are subjected to microwave irradiation until the temperature of the water adjacent the bag reaches a predetermined temperature. While certain portions of the bag may be shielded against direct exposure to such irradiation, the primary factor responsible for the generally uniform heating of the blood, without localized overheating or "hot spots" that might result in hemolysis, is the presence of the surrounding body of water.

A body of water is believed to function as a heat sink to draw excess heat away from the bag and thereby avoid a large temperature gradient between the core liquid and the liquid adjacent to the inner surface of the bag. The water absorbs both microwave energy directly from the source and heat energy from the bag, so that the blood temperature never exceeds that of the water.

In a preferred embodiment, means are provided for circulating the water surrounding the blood bag; however, it is believed that such circulation, while desirable, may not be essential. A temperature detector or probe with its sensing tip alongside the immobilized blood bag, at about the level of the horizontal midplane thereof, detects the temperature of the water and automatically interrupts the heating operation when a selected blood temperature (generally within the range of 94 to 98 degrees F.) is reached.

The blood bag is supported horizontally within the immersion chamber, and the immobilizing means takes the form of a horizontal platen formed of rigid microwave-transmissible material. The platen bears against the upwardly-facing side wall of the horizontally-oriented bag, and retaining springs urge the platen downwardly to hold the blood bag in place. That area of the platen in direct contact with the bag (which is also in generally vertical alignment with the microwave-generating source directly thereabove), as well as selected portions of the platen overlying the outlet fittings of the bag, may be provided with an opaque layer or coating capable of blocking microwave transmission. The effect is to provide shielding for those portions of the bag that are more directly exposed to microwaves and might be heated more quickly than other portions of the bag and its contents.

The apparatus, in its simplest form, may comprise a unit capable of being placed within a conventional microwave oven. Alternatively, the invention contemplates that the apparatus may be part of a microwave oven or heating appliance specifically designed and constructed for rewarming blood.

Other features, advantages, and objects will appear from the specification and drawings.

DRAWINGS

DETAILED DESCRIPTION OF PREFERRED EMBODIMENTS

Figure 1:
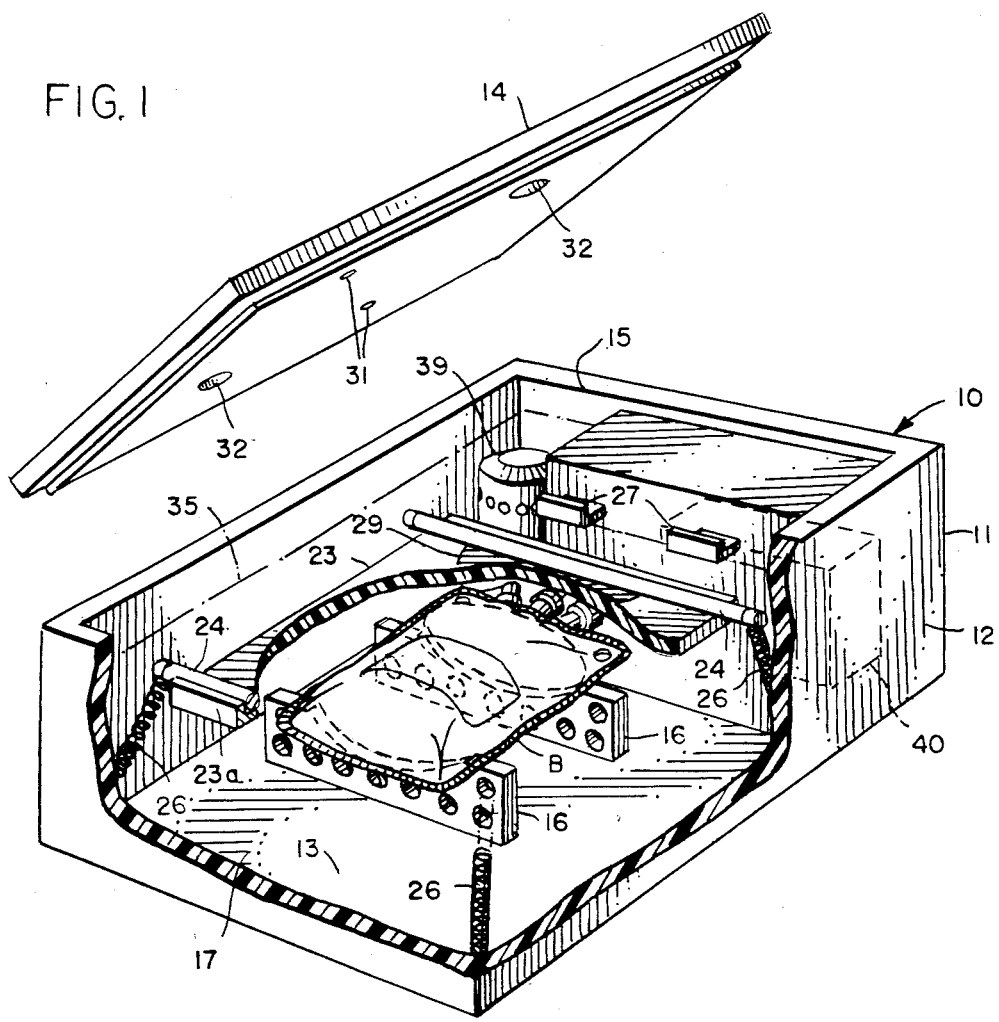
FIG. 1 is a perspective view of an apparatus embodying the present invention, the cover of the apparatus being raised, and wall portions of the apparatus being cut away, to illustrate important structural features and relationships.

Referring to the drawings, the numeral 10 generally designates an apparatus comprising an open-topped housing 11 having side and bottom walls 12 and 13 respectively. The housing is generally rectangular in configuration, although other shapes may be utilized. A cover 14 fits over top opening 15 to seal that opening when the apparatus is in operation.

Support means in the form of a pair of upstanding support or saddle members 16 are disposed within the chamber 17 of the housing. The members 16 are secured to bottom wall 13 and are provided with arcuate upper surfaces 16a for receiving and supporting a blood bag B. The plastic blood-containing bag is entirely conventional and is provided at one end with an outlet port 18 and attached tubing 19 as well as injection and sampling ports 20 and 21. As shown most clearly in FIG. 2, the support members 16 support the bag B in horizontal position well above the surface of bottom wall 13. Apertures 22 are provided in the support members to promote the circulation of fluid within the chamber.

The immobilizing means for holding the bag in place upon saddle members 16 takes the form of a horizontal platen 23 that overlies and firmly engages bag B. The platen is of planar rectangular configuration with horizontal dimensions considerably smaller than those of the chamber 17 of the housing. Like the housing 11 and support members 16, the platen is formed of a rigid material capable of freely transmitting microwaves. Rigid materials such as acrylic polymers and copolymers have been found effective, but other rigid plastic and non-plastic materials capable of transmitting microwave energy may be used. Lips or flanges 23a project upwardly from opposite side edges of the platen, and retaining means in the form of rigid rods or bars 24 (also formed of microwave-transmitting material) fit over the lips 23a as indicated by arrows 25 in FIG. 3. Tension springs 26 formed of a microwave-transmitting plastic, connect the ends of the rods to the lower inside corners of the housing. The length of the springs is such that they are in stretched condition when the parts are assembled as shown in FIG. 1, thereby urging the horizontal platen downwardly into firm engagement with the upper surface of the blood bag B and immobilizing the bag on its supports 16. Brackets 27 project into the chamber from opposite walls to support the rods 24 when they are not in use, as indicated by broken lines in FIG. 2.

Figure 4:
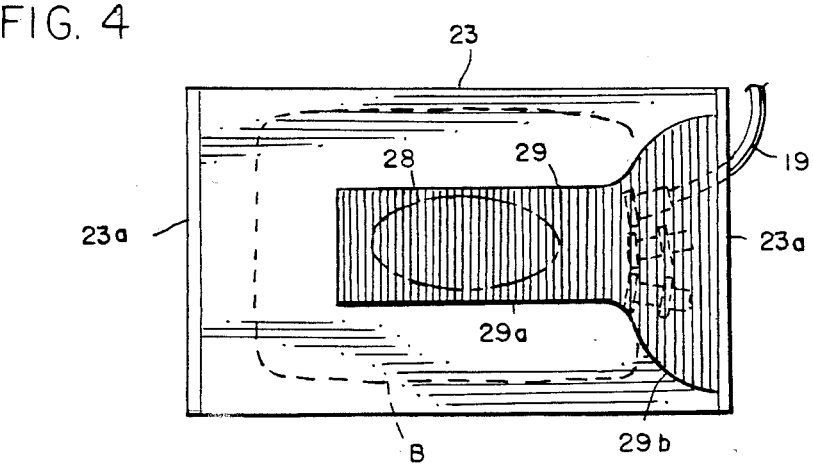
FIG. 4 is a top plan view of the immobilizing platen illustrating its microwave shielding zone in relation to the outline of a blood bag disposed therebeneath.

It will be noted from FIG. 4 that platen 23 has horizontal dimensions larger than the outline of blood bag B. The oval phantom line 28 schematically illustrates the area of direct contact between the underside of the platen and the wall of the blood bag when the apparatus is in use. A defined area 29 of the platen is covered by or contains a layer of material, such as a metal foil or coating, that blocks the transmission of microwaves. Aluminum foil has been found highly effective but other materials or coatings having similar properties may be used. Layer 29 serves as a shield to protect those portions of the blood bag B that might be subject to more rapid heating because of their location in direct alignment with the microwave generating source S when the apparatus is in use (FIG. 2), or because of metal clips or the greater mass of plastic material at the inlet/outlet ports of the bag, or because of the closer proximity to the source S of that portion of the bag in direct contact with platen 23. It will be noted that the radiation shield has a rectangular tongue portion 29a that extends down the longitudinal midplane of the platen and an enlarged end portion 29b that overlies the portion of the bag B equipped with ports 18, 20, and 21 (FIG. 4). Ideally, the width of the tongue portion 29a approximates the width of the zone of contact 28 between platen 23 and bag B.

Cover 14 is provided with vent openings 31 and access openings 32 for the insertion of a conventional temperature-sensing probe 33 connected to suitable switching means 34 for interrupting operation of the microwave generator S when a predetermined temperature has been sensed by the probe. The switching means 34 as well as the generator S may be components of a conventional microwave oven 35 represented in phantom in FIG. 2. Alternatively, the generator, switching means, and probe may be components of a microwave appliance designed specifically for the purpose of rewarming blood. In the embodiment illustrated in the drawings, the cover is provided with two openings 32, either (or both) of which may be used for receiving temperature-sensing probes during operation of the apparatus.

Figure 2:
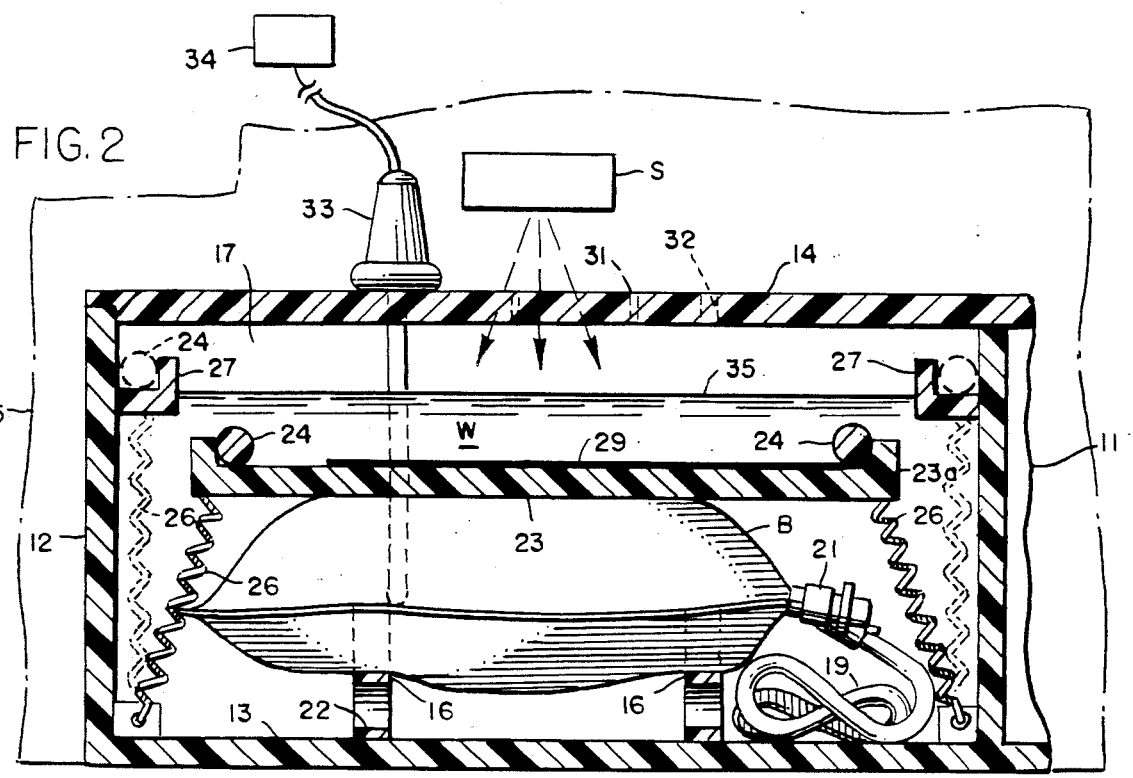
FIG. 2 is a vertical longitudinal sectional view of the apparatus.
Figure 3:
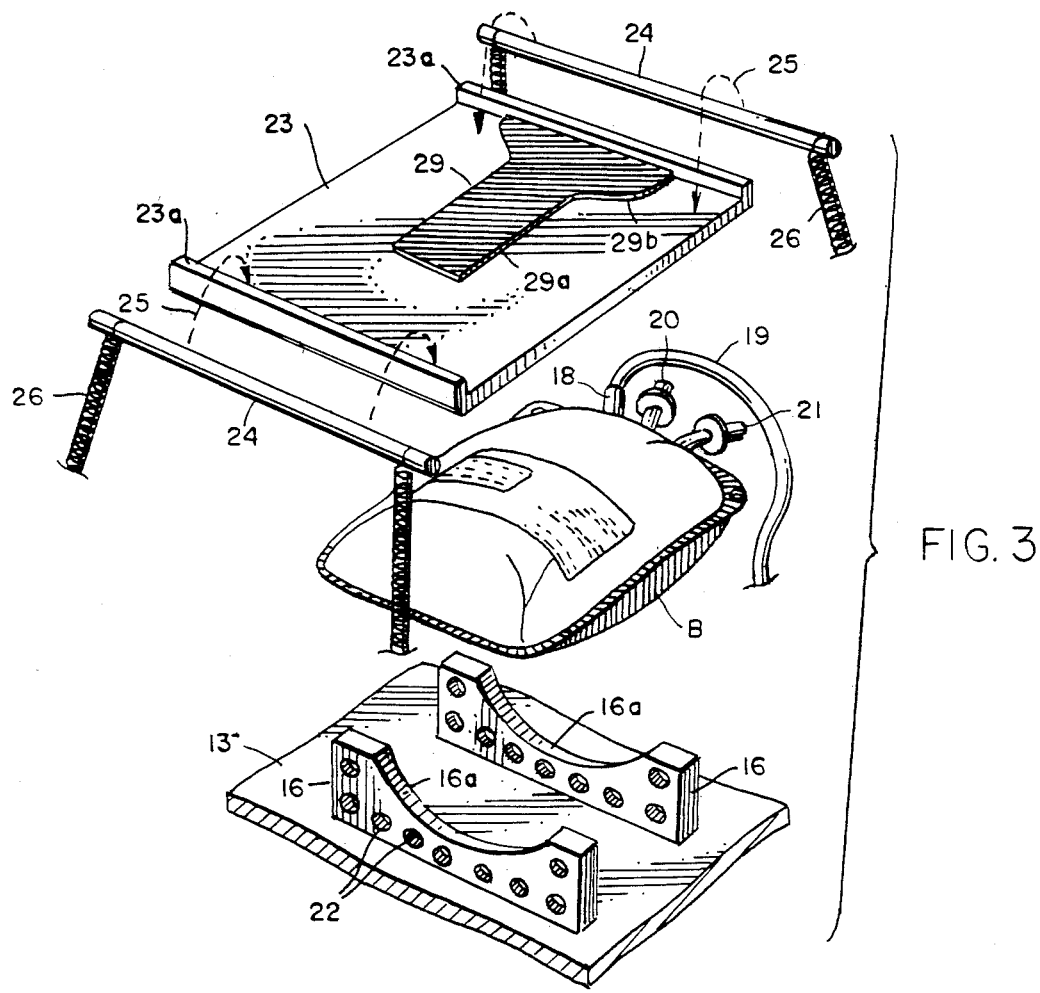
FIG. 3 is an exploded perspective view depicting the blood bag supporting means, a conventional blood bag supported thereby, and the bag-immobilizing means provided by the apparatus of this invention.

In preparation for such operation, chamber 17 is filled with water W to a level indicated at 35 in FIGS. 1 and 2. That level is well above the top of blood bag B and above platen 23. In general it has been found that the water level should be between ½ to 1½ inches above the top of platen 23, with a preferred minimum distance being about 1 inch. Probe 33 is inserted through an opening 32 and is supported by cover 14 with the sensing tip of the probe located alongside bag B at about the horizontal midplane of that bag. Upon activation of the microwave generator S, the contents of the bag and the surrounding water are heated with water functioning as a heat sink to prevent localized overheating of the blood or of the bag itself.

It has been found that unless some means is provided for circulating the water W within the chamber, a limited temperature gradient may develop, with water at a level closer to the generator S being warmed more quickly than water at a more remote location. Accordingly, in the preferred embodiment illustrated in the drawings, a circulating pump 39 located within housing 11 but outside of chamber 17 communicates with the chamber to circulate the water and prevent temperature stratification. The pump may be driven by any suitable power source such as, for example, a spring motor. In the illustration given, the pump is electrically operated with the source of electrical power being a storage battery 40 contained within the housing externally of chamber 17.

While the apparatus shown in the drawings is dimensioned to support a single unit of blood, it is believed apparent that the chamber 17 might be dimensioned to support several bags B for simultaneous rewarming of their contents. It has been found that in the operation of such an apparatus, refrigerated blood (whole blood or packed red blood cells) may be warmed to 94–98 degrees F. in approximately 5 to 6 minutes when immersed in water at room temperature prior to microwave exposure. Slightly longer times (7 to 8 minutes) are required if a unit of fresh frozen plasma must be thawed. Scanning of the units by infrared thermometry immediately following removal from the body of water after microwave exposure has failed to reveal localized overheating. More specifically, it has been found that an apparatus embodying this invention may be readily operated to rewarm banked blood products without degradation of red blood cells or inactivation of clotting factors.

While in the foregoing, I have disclosed embodiments of the invention in considerable detail for purposes of illustration, it will be understood by those skilled in the art that many of these details may be varied without departing from the spirit and scope of the invention.

I claim:

1. A method of rewarming blood contained in a plastic bag in preparation for infusion of such blood, comprising the steps of supporting a blood bag in a housing formed of microwave-transmissible material and containing a volume of water; immobilizing said blood bag within said housing with said immobilized bag being totally immersed in said volume of water; subjecting said water and bag to microwave irradiation until the temperature of the water adjacent said bag reaches a predetermined temperature, and interrupting said irradiation when said predetermined temperature of said water adjacent said bag has been reached.

2. The method of claim 1 in which there is the further step of shielding portions of said bag from direct exposure to such irradiation.

3. The method of claims 1 or 2 in which said bag is supported horizontally within said volume of water.

4. The method of claim 3 in which said irradiation is directed towards said bag and water from above the same.

5. The method of claims 1 or 2 in which said immobilizing step includes contacting and holding said bag in fixed position by means of a submerged platen formed of microwave-transmissible material and interposed between said bag and the source of said irradiation.

6. The method of claim 5 in which said platen extends in a plane substantially normal to a line extending between said bag and the source of said irradiation.

7. The method of claim 6 in which a portion of said platen is provided with an irradiation shield for shielding portions of said bag against direct exposure to said irradiation.

8. The method of claim 1 in which there is the further step of step of removing said bag from said volume of water when said predetermined temperature has been reached.

9. The method of claim 1 in which there is the further step of circulating said volume of water about said bag during said irradiation step.

10. An apparatus for rewarming blood contained in a plastic bag, comprising a housing formed of rigid microwave-transmissible material having bottom and side walls defining an open-topped chamber; said chamber being adapted to support a body of water having its surface at a predetermined level therein; supporting means within said chamber for supporting a blood bag below said predetermined level, above said bottom wall, and spaced from said side walls; and holding means disposed within said chamber below said predetermined water level for engaging and holding said blood bag in fixed position on said supporting means; said holding means having at least portions thereof formed of microwave-transmissible material.

11. The apparatus of claim 10 in which said holding means comprises a platen formed of rigid microwave-transmissible plastic material.

12. The apparatus of claim 11 in which said platen includes a microwave-impervious shielding layer along a surface portion thereof.

13. The apparatus of claim 12 in which said portion of said surface providing said shielding layer encompasses an area of said platen that engages a blood bag for holding it in place on said supporting means.

14. The apparatus of claim 12 in which said portion of said surface providing said shielding layer encompasses an area of said platen that overlies an end portion of said bag having inlet/outlet means.

15. The apparatus of claim 12 in which said shielding layer comprises a metal foil.

16. The apparatus of claim 11 in which said holding means includes restraining means connecting said platen to said housing for urging said platen into contact with a blood bag supported by said supporting means.

17. The apparatus of claim 16 in which said restraining means comprises tension springs extending between said platen and said housing.

18. The apparatus of claim 17 in which said tension springs are formed of microwave-transmissible material.

19. The apparatus of claim 10 in which said housing includes a vented cover formed of microwave-transmissible material.

20. The apparatus of claim 10 in which temperature-sensing means is supported within said chamber between said holding means and said supporting means for sensing the temperature of the water alongside a bag supported by said holding means.

21. The apparatus of claim 20 in which a microwave generator is disposed above said housing; said sensing means being operatively connected to said generator for interrupting operation of the same when the sensed temperature reaches a predetermined level.

22. The apparatus of claim 10 in which circulating means are provided in said chamber for circulating the water contained therein.

* * * * *